United States Patent [19]

Dorai et al.

[11] Patent Number: 5,130,470
[45] Date of Patent: Jul. 14, 1992

[54] POLYMERIZATION OF TETRAHYDROFURAN USING A FLUORINATED ACIDIC CATALYST AND MALEIC ACID/MALEIC ANHYDRIDE MIXTURE AS MOLECULAR WEIGHT CONTROL AGENT

[75] Inventors: Suriyanarayan Dorai, Lockport; Willard L. Quon, East Amherst, both of N.Y.; Kirk M. Schall, Ponca City, Okla.; Gary A. Hida, Wilmington, Del.

[73] Assignee: E. I. Du Pont de Nemours and Company, Wilmington, Del.

[21] Appl. No.: 676,065

[22] Filed: Mar. 27, 1991

[51] Int. Cl.$^5$ .............................................. C07C 67/26
[52] U.S. Cl. ..................................... 560/200; 560/198; 560/204; 568/617
[58] Field of Search ................... 560/200, 198, 204; 568/617

[56] References Cited

U.S. PATENT DOCUMENTS 4,259,531  3/1981  Huchler et al. ..................... 568/617

Primary Examiner—Jose G. Dees
Assistant Examiner—Vera C. Clarke

[57] ABSTRACT

A process for polymerizing tetrahydrofuran using a fluorinated resin containing sulfonic acid groups a trifluoromethane sulfonic acid as catalyst and a mixture of maleic acid and maleic anhydride as weight control agent. The product has the formula $$HOC-CH=CH-C(O-(CH_2)_4)_nO-C-CH=CH-C-OH$$

(with $C=O$ groups at each carbonyl)

which can be hydrogenated to produce polytetramethylene ether glycol. The preferred molecular weight range of the polytetramethylene ether glycol is 600 to 4,000.

6 Claims, No Drawings

POLYMERIZATION OF TETRAHYDROFURAN USING A FLUORINATED ACIDIC CATALYST AND MALEIC ACID/MALEIC ANHYDRIDE MIXTURE AS MOLECULAR WEIGHT CONTROL AGENT

FIELD OF THE INVENTION

The present invention relates to the polymerization of tetrahydrofuran to polytetramethylene ether glycol using a fluorinated resin containing sulfonic acid groups as the catalyst and a molecular weight control agent which is a substantially equimolar mixture of maleic acid and maleic anhydride.

BACKGROUND OF THE INVENTION

Polytetramethylene ether glycol is a commodity in the chemical industry, widely used to form segmented copolymers with polyfunctional urethanes and polyesters. It is commonly prepared by reacting tetrahydrofuran with a strong acid catalyst such as fluorosulfonic acid and then quenching the product with water.

While this process has been proved to be quite satisfactory, it is not as efficient as desired because the acid catalyst cannot be recovered and reused. Moreover, disposal of the spent acid catalyst is a problem because of its toxicity and corrosiveness.

More recently, as described in U.S. Pat. No. 4,120,903, it was found that polytetramethylene ether glycol can be prepared from tetrahydrofuran using a catalyst which is a polymer containing pendant fluorosulfonic acid groups and a chain terminator which is water or 1,4-butane diol. The nature of the catalyst permits its reuse, thereby eliminating the disposal problems, and the catalyst's lack of solubility in the reaction mass makes it easy to separate the catalyst from the product at the end of the polymerization reaction. This very low solubility also minimizes loss of catalyst as the reaction proceeds. However, this process produces a product, polytetramethylene ether glycol, having a molecular weight of 10,000 or more, while the commercial products generally have molecular weights of less than 4,000 with the majority of commercial products having a number average molecular weight of either 1,000 or 2,000.

More recently U.S. Pat. No. 4,163,115 disclosed that the molecular weight of the polytetramethylene ether glycol product, when using a catalyst which is a fluorinated resin containing sulfonic acid groups, can be controlled by adding an acylium ion precursor to the reaction medium. The acylium ion precursors were aryl halides and anhydrides of carboxylic acids whose carboxylic acid moieties contain 1 to 36 carbon atoms and especially those of 1–4 carbon atoms. Acetic anhydride, propionic anhydride and formic-acetic anhydride were specifically illustrated. Examples 10–13 of the patent disclose the use of mixtures of acetic anhydride and acetic acid as molecular weight control agents. The reaction product is an ester capped polytetramethylene ether which is reacted with an alkanol such as methanol to provide the final product polytetramethylene ether glycol which, in the preferred case, yields methyl acetate as a by-product.

SUMMARY OF THE INVENTION

The present invention relates to the polymerization of tetrahydrofuran using as catalyst a polymer containing pendant sulfonic acid groups or trifluoromethane sulfonic acid in the presence of maleic and maleic anhydride to control molecular weight of the product. The reaction product has the formula

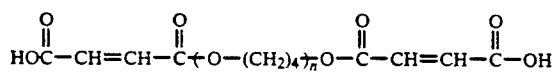

which can be catalytically reduced with hydrogen to produce tetramethylene ether glycol and butane diol, thereby eliminating by-product formation.

DETAILED DESCRIPTION OF THE INVENTION

The present invention involves preparing dimaleate esters of polytetramethylene ether glycol segments having a molecular weight of about 600 to 4,000. The polytetramethylene ether glycol maleate is then reduced to polytetramethylene ether glycol and 1,4-butanediol with hydrogen using a catalyst such as supported palladium.

In the process, the nature of the polymeric catalyst permits its ready reuse, thereby eliminating the disposal problem, and the catalyst's low solubility in the reaction mass makes it easy to separate at the end of the polymerization reaction. This low solubility also minimizes loss of catalyst as the polymerization reaction proceeds.

The fact that the maleic acid ester end caps after hydrogenation windup as part of the polymethylene ether glycol eliminates the disposal problems associated with using other acylium ion precursors which after reaction wind up as a by-product such as methyl acetate which represents a loss and further need to be disposed of.

The reaction proceeds as follows:

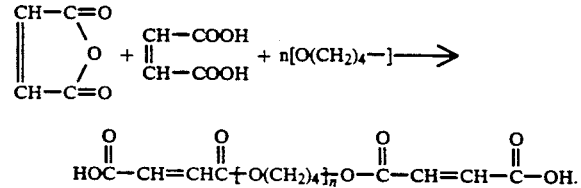

If the amount of maleic acid is increased above equimolar with maleic anhydride, the reaction produces water which in small amounts has not been found to be a problem with carrying out the reaction.

As the ratio of maleic anhydride to maleic acid varies, the molecular weight of the product increases with the decreasing amount of maleic acid. When no maleic acid is used, the molecular weight increase is excessive.

The mole ratio of maleic anhydride/maleic acid mixture to tetrahydrofuran in the reaction mass should be about 1:1 to produce polytetramethylene glycol dimaleate of the desired molecular weight, i.e., number average molecular weight of 600 to 4,000.

The temperature in the reaction medium is generally kept in the range of 20° to 65° C.

In either batch or continuous mode, the process is ordinarily run at atmospheric pressure, but reduced or elevated pressure may be used for any of various reasons such as to aid in controlling the temperature of the reaction mass during the reaction.

It is preferable to exclude oxygen from the reaction zone. This can be done by running the process in an inert atmosphere such as dry nitrogen or argon.

The polymerization process of the present invention can be run in a batch mode or continuously.

When run in a batch mode, the desired amounts of tetrahydrofuran, maleic acid, maleic anhydride and catalyst are placed in a reactor and stirred while the desired reaction conditions are maintained. When the reactions are finished, the catalyst and the reaction mass are separated and the product, polytetramethylene ether glycol dimaleate, is then separated from the remainder of the reaction mass. When run continuously, the process is similarly run preferably in a back-mixed slurry reactor, with continuous stirring with continuous addition of reactants and continuous removal of product. Alternatively, the reaction can be run in a pipeline reactor.

In a pipeline reactor, the process is run under plug-flow conditions whereby premixed reactants move through the reactor which is packed with catalyst. Preferably the movement is continuous, with little or no mixing of the initial with partially converted reactants as they move along.

A pipeline reactor is preferably oriented vertically, with the reactants moving upwardly through the catalyst bed, which tends to suspend the catalyst, make the flow of reactants freer and prevent channeling as compared to the case where the reactants are fed downwardly through the reactor.

In either the slurry or pipeline reactor, it is preferable to adjust the temperature in the reaction zone, the concentration of reactants in the reaction zone and the flow rate of the reactants into and out of the reaction zone so that about 5 to 85%, preferably 15 to 60% and even more preferably 15 to 40%, of the tetrahydrofuran is converted to the maleate capped polytetramethylene ether glycol on each pass through the reactor. The effluent of each pass, after the product has been removed, can be recycled to the reactor. It is also preferable that at least about 40% by weight and even more preferably about 80 to 90% of the maleic acid/maleic anhydride mixture be consumed on each pass of the reactants through the reactor. With proper adjustment of concentrations of reactants in the feed stream, of flow rates and of temperature, all of these conditions can ordinarily be obtained with a residence time in the reactor of 10 minutes to 2 hours, preferably 15 to 60 minutes, even more preferably 20 to 45 minutes.

Residence time (in minutes) is determined by measuring the volume (in milliliters) of the free space in the reaction zone and then dividing this figure by the flow rate (in milliliters per minute) of the reactants through the reactor. In a slurry reactor, the reaction zone is the entire volume of the liquid reaction mixture; in a pipeline reactor the reaction zone is the zone containing the catalyst.

In the batch mode the process is ordinarily run for 1 to 24 hours.

On completion of the polymerization reaction, the catalyst can be separated from the reaction mass by filtration, decantation or centrifugation and reused. If the process is run in a continuous fashion, the catalyst can simply be allowed to remain in the reactor while fresh reactants are fed in and the product is removed.

In either the batch or continuous mode, after removal of the catalyst, the product is separated from the reaction mass by extracting residual unreacted tetrahydrofuran, maleic acid/maleic anhydride from the reaction mass by stripping the reaction mass with steam or an inert gas such as nitrogen.

The tetrahydrofuran used as the reactant in the process of the present invention can be any of those commercially available. It preferably has a water content of less than about 0.001% by weight and a peroxide content of less than 0.002% by weight. Preferably the tetrahydrofuran contains a minor amount of an oxidation inhibitor such as butylated hydroxytoluene to prevent formation of unwanted by-products and color.

If desired 0.1 to 50% by weight, of the tetrahydrofuran, of an alkyl derivative of tetrahydrofuran, copolymerizable with tetrahydrofuran can be used as a co-reactant. Such an alkyl tetrahydrofuran can be represented by the structure:

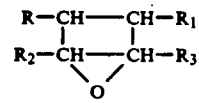

where any one of —R, —$R_1$, —$R_2$ or —$R_3$ is an alkyl radical of 1 to 4 carbon atoms, the remaining —Rs being hydrogen.

Illustrative of such alkyl furans are 2-methyl tetrahydrofuran and 3-methyl tetrahydrofuran.

The polymeric catalyst used in the process of the present invention is a polymer of an ethylenically unsaturated monomer (a) containing groups such that the final polymer will contain groups of the formulae

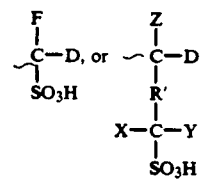

wherein ∼ represents the polymer chain or a segment thereof;

D is hydrogen, an aliphatic or aromatic hydrocarbon radical of 1 to 10 carbon atoms, a halogen atom or a segment of the polymer chain;

X and Y are hydrogen, a halogen atom, an aliphatic or aromatic hydrocarbon radical of 1 to 10 carbon atoms, but at least one must be fluorine;

R' is a linear or branched linking group having up to 40 carbon atoms in the principal chain; and Z is hydrogen, halogen or an aliphatic or aromatic hydrocarbon radical of 1 to 10 carbon atoms or fluorine, or a copolymer of monomer (a) with at least one other copolymerizable ethylenically unsaturated monomers (b).

The linking group defined by R' in the formula above can be a homogeneous one such as an alkylene radical or a heterogeneous one containing one or more alkylene ether radicals. In the preferred catalysts, this linking radical contains 1 to 20 carbon atoms in the principal chain. In the especially preferred catalyst, R is a radical of the structure

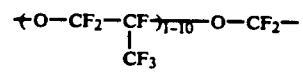

Illustrative of monomer (a) are such monomers as trifluorovinyl sulfonic acid, linear or branched chain vinyl monomers containing sulfonic acid group precursors and perfluoroalkylvinyl ethers containing sulfonic acid precursors.

Illustrative of monomer (b) are such monomers as ethylene, styrene, vinyl chloride, vinyl fluoride, vinylidene fluoride, chlorotrifluoroethylene, bromotrifluoroethylene, vinyl ethers, perfluoroalkylvinyl ethers containing 1-6 carbon atoms in the alkyl group, butadiene, tetrafluoroethylene and hexafluoropropylene.

The homopolymerization or copolymerization used to form the catalyst can be done according to the procedures described in U.S. Pat. No. 3,784,399 to George Pruckmayr, and the patents cited therein. Monomers are selected to provide a polymer having the desired equivalent weight.

Generally the polymeric catalysts used in the present invention have equivalent weights of 950 to 1,500, preferably 1,100 to 1,300. The equivalent weight, as applied to catalysts as used herein is that weight in grams which contains one gram equivalent of sulfonic acid groups, and can be determined by titration.

Generally the catalysts have solublities such that less than 5% by weight dissolves in the reaction mass at reactions temperatures of 20° to 65° C. when the reaction is run in a batch mode. This solubility can be determined gravimetrically.

It is preferred that the solubility of the polymeric catalyst be as low as possible because this minimizes catalyst loss and permits the process to be run for longer periods without catalyst replenishment. Preferably, the solubility of the catalyst is no more than 1% by weight and even more preferably is below the threshold of detection with present analytical techniques.

The polymeric catalyst should be effectively free of functional groups other than —SO$_3$H groups, which might interfere with the polymerization reaction. "Effectively free" means the catalyst may contain a small number of such groups, but not so many that the reaction is adversely affected or the product contaminated. Illustrative of such groups are carboxyl groups, hydroxyl groups and amino groups.

Catalysts whose polymer chains are perfluorocarbon monomers are preferred for use in the process of the present invention. Illustrative of monomers (b) suitable for use in producing the preferred polymer chains are tetrafluoroethylene, hexafluoropropylene, chlorotrifluoroethylene, bromotrifluoroethylene and perfluoroalkylvinyl ethers. Mixtures of monomers can be used.

Even more preferred as catalysts are copolymers of tetrafluoroethylene or chlorotrifluoroethylene and a monomer of the structure (monomer (c)):

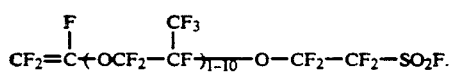

These copolymers are prepared in the sulfonyl fluoride form and then are hydrolyzed to the acid form as described in U.S. Pat. No. 3,692,569.

Most preferred as polymeric catalysts are copolymers of tetrafluoroethylene and monomer (c) in which the respective monomer unit weight ratios are 50-75/25-50, such copolymers having equivalent weights of 1,100, 1,150 and 1,500, are sold by E. I. du Pont de Nemours and Company as Nafion ® perfluorosulfonic acid resin. Alternatively, trifluoromethane sulfonic acid may be used as the catalyst.

The catalyst is present in the reaction mass in a catalytically effective amount, which in the usual case means a concentration of about 0.01% to 30% by weight of the reaction mass, preferably 0.05 to 15%, and even more preferably 0.1% to 10%.

The product polytetramethylene ether glycol dimaleate can be directly converted to polytetramethylene ether glycol by hydrogenation. Generally the hydrogenation is carried out using a hydrogen pressure of 500 to 3000 psi and a temperature of 150° to 300° C. being the preferred range. Suitable hydrogenation catalysts include nickel and the noble metals.

EXAMPLE 1

A feed composition consisting of 810 g dry tetrahydrofuran, 21.1 g maleic anhydride and 25.5 g maleic acid was prepared. A stainless steel reactor fitted with an agitator and heated by a heating mantle was filled with approximately 100 g of NR-55 catalyst. NR-55 catalyst which contains 70 wt.% of fluorocarbon polymer having SO$_3$H end groups. The above feed composition was fed to the reactor at a rate of 0.4 g per minute. The reactor temperature was maintained at 50°. The reactor was on stream for 40 days during which time the conversion of tetrahydrofuran ranged from 15 to 18% and the number average molecular weight of the polytetramethylene ether glycol dimaleate varied from 1,500 to 2,000.

EXAMPLE 2

A series of runs were made using trifluoromethane sulfonic acid (Triflic acid) as catalyst. The results are reported in the table below.

TABLE

| | Weight in Grams | | | | |
|---|---|---|---|---|---|
| THF | Triflic Acid | Maleic Acid | Maleic Anhydride | Temp. °C. | Time Hrs/Mol. Wt./Conv |
| 200 | 16.0 | — | — | 60 | 2/>10,000/16.0 |
| 200 | 15.8 | 5.5 | — | 60 | 2/No Terathane ® |
| 200 | 16.2 | — | 5.5 | 60 | 2/>10,000/13.5 |
| 200 | 16.2 | 6.41 | 5.34 | 60 | 1.0/3543/11.8 |
| | | | | | 1.5/3046/41.0 |
| | | | | | 2.5/2796/43.3 |
| | | | | | 3.5/2764/46.7 |
| 160 | 12.96 | 7.18 | 6.06 | 60 | 1.0/2653/15.1 |
| | | | | | 1.5/2071/25.6 |
| | | | | | 2.0/1536/33.6 |
| | | | | | 2.5/1464/42.6 |
| | | | | | 3.3/1510/43.9 |
| | | | | | 4.0/1703/57.8 |
| | | | | | 4.5/1855/51.0 |
| 135 | 4.4 | 13.35 | 12.20 | 60 | 0.75/252/12.0 |

EXAMPLE 3

This example illustrates the hydrogenation step of a polytetramethylene ether glycol, prepared by a model polymerization of tetrahydrofuran and succinic anhydride with Triflic acid catalyst. (Maleic esters are just as easily reduced.) The NMR molecular weight of the polytetramethylene ether glycol succinate was 650. 12 Grams of this material were sent for pressure hydrogenation.

| | Part A: |
|---|---|
| 12 g | PTMEG succinate |
| 10 g | isopropanol |
| 0.5 g | catalyst (Pd/Re on carbon) |
| | Part B: |
| 1 g | potassium tert.-butoxide |

| | |
|---|---|
| 82 g | isopropanol |

Parts A and B were added to a stainless steel hydrogenation bomb, the bomb was evacuated, flushed with nitrogen and pressurized with hydrogen to a pressure of 2000 psig. Hydrogenation was carried out at 250° C. for 8 hrs. This is probably excessive, but the product was completely hydrogenated, and did not contain any more ester groups (carbonyl absorption band in IR absent).

We claim:

1. A process for preparing maleate ester end-capped polytetramethylene ether glycol or maleate ester end-capped polytetramethylene ether glycol copolymer comprising (a) bringing together at a temperature of about 20° to 65° F., (1) tetrahydrofuran and, alone or with, up to 50% by weight of the tetrahydrofuran of a copolymerizable alkyl tetrahydrofuran of the structure

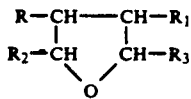

where any one of R, $R_1$, $R_2$ and $R_3$ is an alkyl radical of 1 to 4 carbon atoms, the remaining Rs being hydrogen, (2) a mixture of maleic acid and maleic anhydride, (3) as catalyst, trifluoromethane sulfonic acid, or a polymer having a solubility of less than 5% by weigh in the reaction medium as run in a batch mode of an ethylenically unsaturated monomer (a) containing groups such that the final polymer contains groups of the formulae

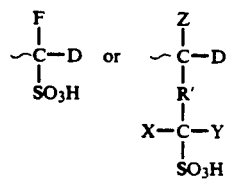

wherein ~ represents the polymer chain or a segment thereof;

D is a hydrogen, an aliphatic or aromatic hydrocarbon radical of 1 to 10 carbon atoms, a halogen or a segment of the polymer chain;

X and Y are hydrogen, halogen or an aliphatic or aromatic radical of 1 to 10 carbon atoms, but at least one of X or Y must be fluorine;

R is a linear or branched linking group having up to 40 carbon atoms in the principal chain; and Z is a hydrogen, halogen or an aliphatic or aromatic radical of 1 to 10 carbon atoms;

wherein the polymer is a homopolymer of a) or a copolymer thereof with one or more ethylenically unsaturated monomers (b) which form the polymer chain, the polymers having an equivalent weight of from about 950 to about 1,500 and being effectively free of functional groups which interfere with the reactions; and (b) separating the resulting polytetramethylene ether glycol maleate product from the reaction mass.

2. The process of claim 1 wherein the mole ratio of the maleic acid/maleic anhydride mixture to tetrahydrofuran in the reaction mixture is about 1:1.

3. The process of claim 2 wherein the catalyst has a solubility in the reaction mass of less than 5% by weight when run in a batch mode at 20° to 65° C.

4. The process of claim 3 wherein the catalyst is a copolymer of monomer (a) and a perfluorocarbon monomer.

5. The process of claim 3 wherein the catalyst is a copolymer of tetrafluoroethylene or chlorotrifluoroethylene and a monomer represented by the structure

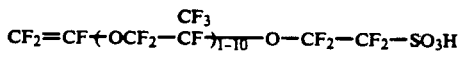

said monomer units being present in weight ratios of 50-75/25-50, respectively.

6. The process of claim 3 wherein it is conducted in a continuous fashion.

* * * * *